United States Patent
Khadduri et al.

(10) Patent No.: US 6,662,629 B2
(45) Date of Patent: Dec. 16, 2003

(54) PROPELLANT TEST APPARATUS AND METHOD

(75) Inventors: Farid M. Khadduri, Bethesda, MD (US); Guy Bruce Spear, Orlean, VA (US)

(73) Assignee: Atlantic Research Corporation, Gainsville, VA (US)

( * ) Notice: Subject to any disclaimer, the term of this patent is extended or adjusted under 35 U.S.C. 154(b) by 11 days.

(21) Appl. No.: 10/120,830

(22) Filed: Apr. 12, 2002

(65) Prior Publication Data

US 2003/0192364 A1 Oct. 16, 2003

(51) Int. Cl.⁷ .............................................. G01N 33/22
(52) U.S. Cl. ..................... 73/35.17; 73/35.14
(58) Field of Search .......................... 73/35.14, 35.17, 73/35.15, 35.16, 865.6, 167, 116

(56) References Cited

U.S. PATENT DOCUMENTS

| | | |
|---|---|---|
| 3,165,924 A | 1/1965 | Wolff |
| 3,267,721 A | 8/1966 | Jacobs et al. |
| 3,580,049 A | 5/1971 | Cardwell et al. |
| 3,701,278 A | 10/1972 | Askins et al. |
| 4,349,200 A | 9/1982 | Wakefield |
| 4,379,405 A | 4/1983 | Engeler et al. |
| 4,523,475 A | 6/1985 | Bills, Jr. et al. |
| 4,554,823 A | 11/1985 | Lilley |
| 4,759,215 A | 7/1988 | Atchley et al. |
| 5,052,817 A | 10/1991 | Bement et al. |
| 5,419,119 A | 5/1995 | Obney |

*Primary Examiner*—John E. Chapman
(74) *Attorney, Agent, or Firm*—Nixon & Vanderhye, P.C.; Frank P. Presta

(57) ABSTRACT

A test apparatus and method for a solid propellant, comprising a combustion chamber for the solid propellant, an igniter for igniting propellant in the combustion chamber, and an exhaust housing having a primary exhaust channel extending from the combustion chamber to an exit nozzle. A supplemental exhaust channel is connected to the primary exhaust channel, and a valve controls the size of the supplemental exhaust channel to selectively vary the flow of propellant gases therethrough, thereby to selectively vary the combustion chamber pressure to enable the testing of the burning characteristics of the propellant over a wide pressure range independent of the burning surface area of the propellant. In a further embodiment, an auxiliary exhaust channel closed by a burst disk is connected to the primary exhaust channel. The burst disk is constructed to fail at a predetermined pressure to enable exhaust gases to be vented through the auxiliary exhaust channel in the event the gas pressure in the primary exhaust channel exceeds the predetermined pressure.

10 Claims, 5 Drawing Sheets

PROPELLANT TEST APPARATUS AND METHOD

BACKGROUND OF THE INVENTION

The present invention relates to apparatus and method for testing solid propellants and, more particularly, to a new and improved apparatus and method for testing solid propellants over a wide pressure range that is independent of the burning surface area of the propellant.

In previously used solid propellant test apparatus, the burning characteristics of the propellant have been tested under different pressures by varying the burning surface area of the propellant. While such test apparatus has performed satisfactorily, it has not been completely satisfactory in that it has only been possible to test the burning characteristics of the propellant over a limited number of pressures determined by the different burning surface areas of the propellant. A need has arisen, therefore, for a new and improved propellant test apparatus that is capable of testing solid propellants of different types over a wide pressure range independent of the burning surface area of the propellants. The test apparatus of the present invention fills this need.

SUMMARY OF THE INVENTION

The new and improved propellant test apparatus and method of the present invention provides a supplemental exhaust channel for the gases of the burning propellant being tested in addition to the normal or primary exhaust channel and exit nozzle at the end of the exhaust housing for the test apparatus. The flow of propellant gases through the supplemental exhaust channel is controlled by a valve of any suitable construction which can be controlled to vary the size of the supplemental exhaust channel over a wide range from fully open to fully closed. By varying the size of the supplemental exhaust channel, the flow of exhaust gases through the exit nozzle and the supplemental exhaust channel can be varied to control the combustion chamber pressure on the solid propellant being tested over a wide range that is independent of the burning surface area of the propellant. Accordingly, it is possible with the propellant test apparatus of the present invention to test the burning characteristics of different types of propellants over a wide pressure range that can be easily selectively controlled.

DESCRIPTION OF THE PREFERRED EMBODIMENTS

Figure 1:
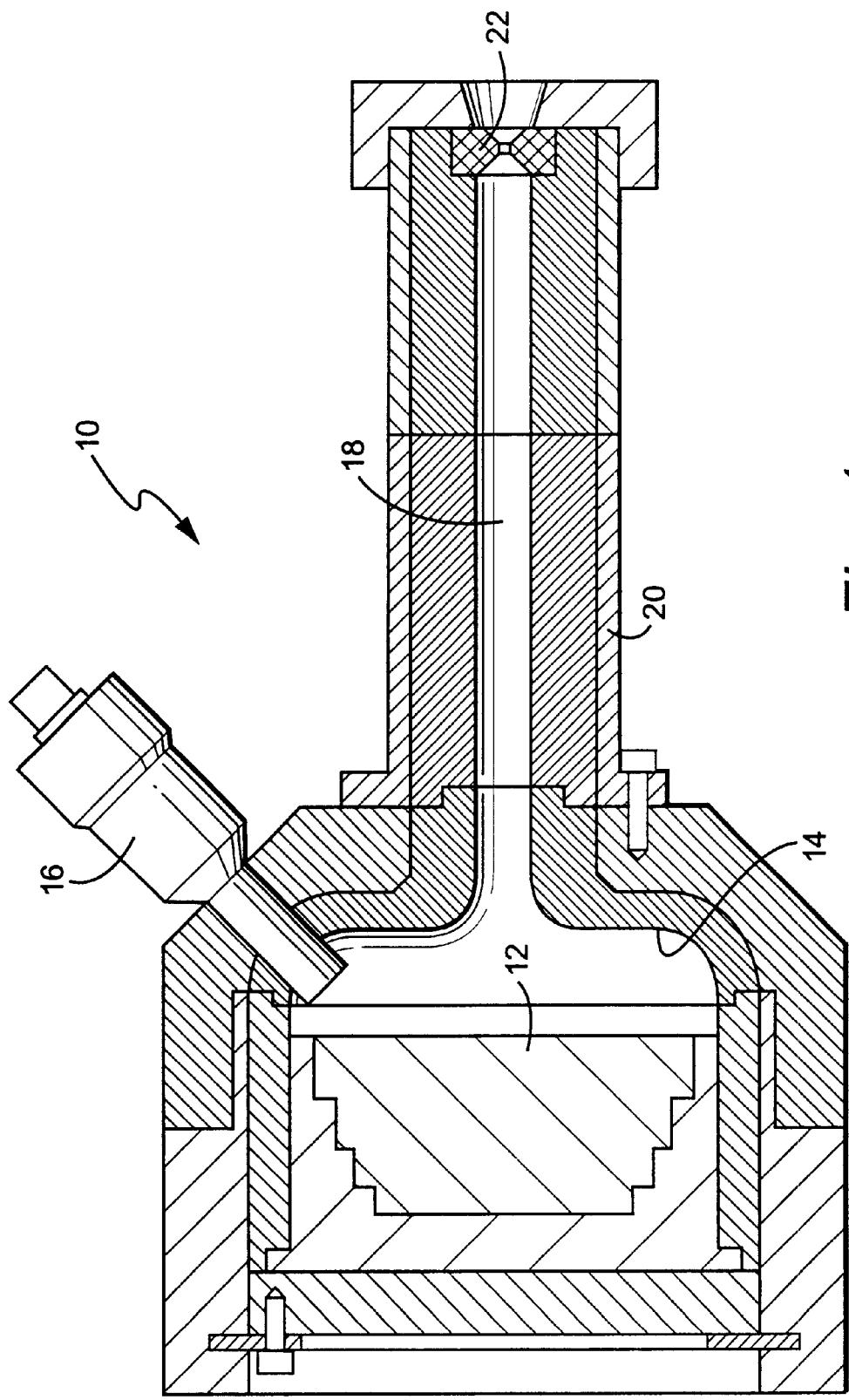
FIG. 1 is a side elevational view in section of a propellant test apparatus that is known in the prior art.

FIG. 1 illustrates a test apparatus 10 for a solid propellant 12 of the type that is currently used and known in the prior art. The test apparatus 10 comprises a combustion chamber 14 in which the propellant 12 is mounted, an igniter 16 of any suitable type extending into the combustion chamber 14 for igniting the propellant 12, an exhaust channel 18 in an exhaust housing 20 extending from the combustion chamber 12 to an exit nozzle 22 of any suitable construction.

In order to test the burning characteristics of the solid propellant 12 under different pressures, the propellant is formed of a stepped construction such that the burning surface area will be reduced to lower the combustion chamber pressure as the propellant burns into smaller stepped surface areas. It will be readily seen, therefore, that this prior art test apparatus can only test the burning characteristics of the propellant over a limited pressure range determined by the size of the burning surface areas of the propellant.

Figure 2:
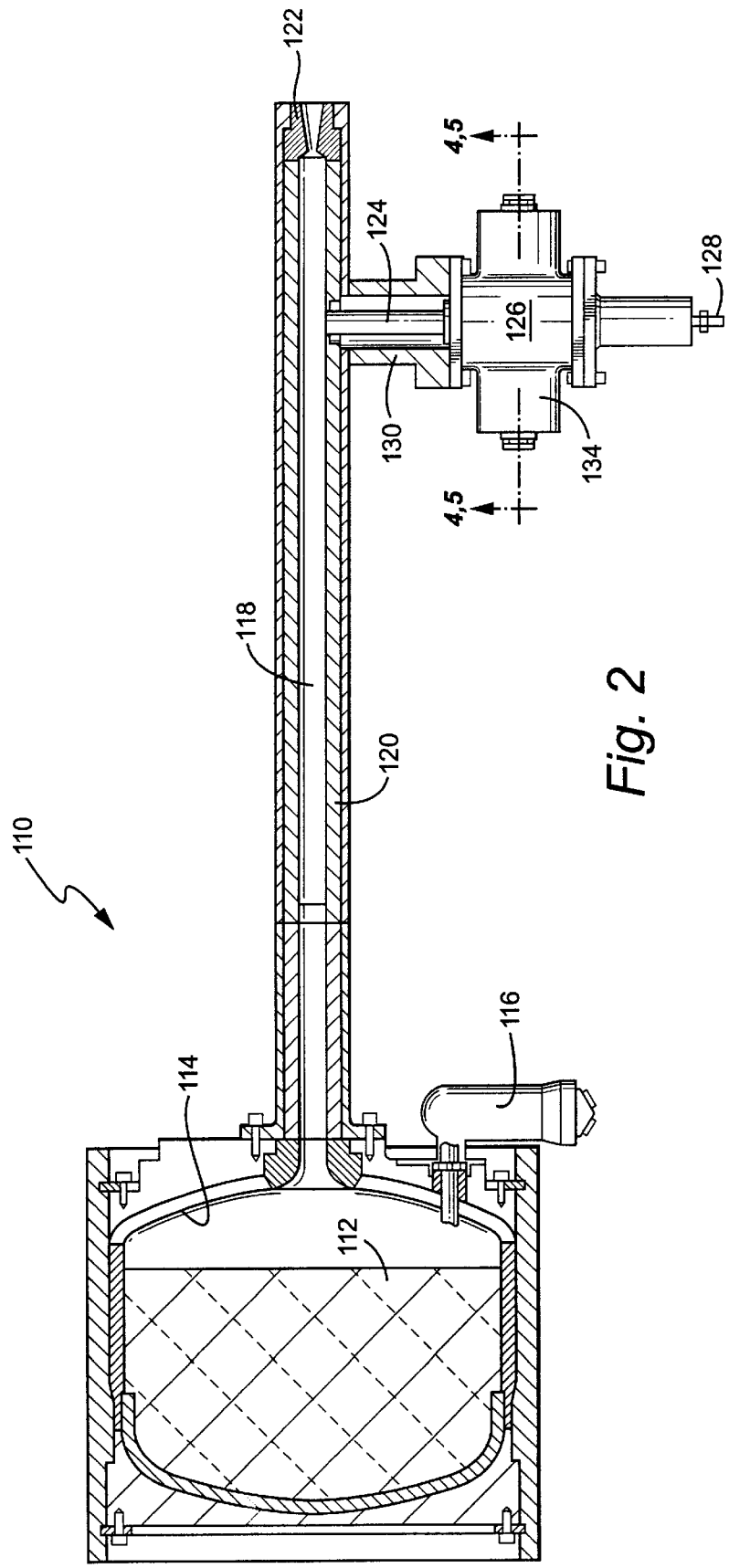
FIG. 2 is a side elevational view in section of a first embodiment of the new and improved propellant test apparatus of the present invention.

FIG. 2 illustrates a first embodiment of the new and improved propellant test apparatus 110 of the present invention which comprises a combustion chamber 114 in which a solid propellant 112 of any suitable or desired type is mounted in any suitable manner, and an igniter 116 of any suitable type extending into the combustion chamber 114 for igniting the propellant 112. A primary exhaust channel 118 extends through an exhaust housing 120 from the combustion chamber 114 to an exit nozzle 122 of any suitable construction.

A supplemental exhaust channel 124 extends from the primary exhaust channel 118 through an exhaust valve 126 of any suitable construction to a supplemental exhaust opening 128. The exhaust channel 124 is formed in a housing 130 connected at one end to the exhaust housing 120 and at the other end to the exhaust valve 126. The valve 126 is constructed to be selectively movable to control the size of the supplemental exhaust channel 124 and thus the amount of flow of the exhaust gases from the burning propellant 112 through the supplemental exhaust opening 128. By controlling the flow of exhaust gases from the burning propellant 112 through the supplemental exhaust opening 128 in addition to the normal flow through the exit nozzle 122, the combustion chamber pressure on the burning propellant 112 can be varied over a wide range to enable the burning characteristics of the propellant 112 to be tested at many different pressures that are independent of the burning surface area of the propellant. Accordingly, the new and improved propellant test apparatus 110 is a significant improvement over the prior art apparatus shown in FIG. 1.

Figure 4:
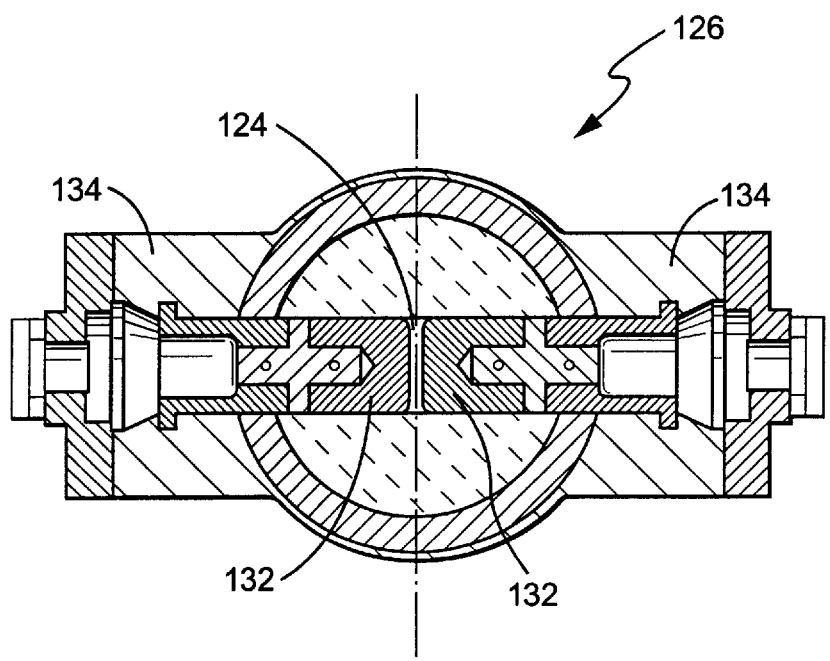
FIG. 4 is an enlarged plan view of one embodiment of a valve for the supplemental exhaust channel taken substantially along line 4—4 in FIG. 2, showing the valve in a fully closed position.
Figure 5:
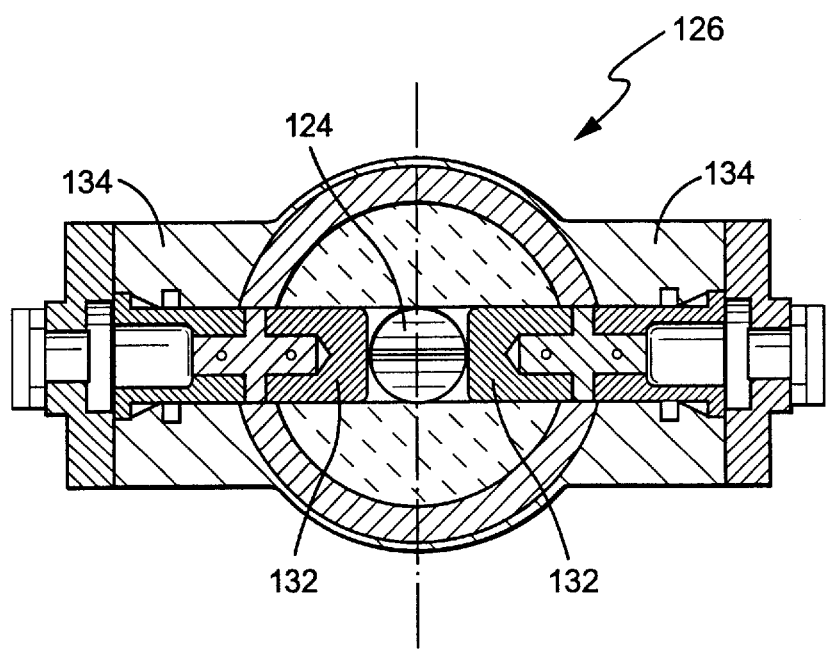
FIG. 5 is a sectional view similar to that in FIG. 4, showing the valve for the supplemental exhaust channel in a fully open position.

FIGS. 4 and 5 illustrate one embodiment of an exhaust valve 126 for controlling the size of the supplemental exhaust channel 124 shown in FIG. 2. The exhaust valve 126 comprises a pair of opposed pistons or valve members 132 that are slideably mounted in housings 134 for movement between the positions shown in FIG. 4 wherein they close the supplemental exhaust channel 124 and the positions shown in FIG. 5 wherein they are disposed outside of the supplemental exhaust channel 124 such that it is fully open. The movement of the pistons 132 may be controlled in any suitable or well known manner.

Figure 6:
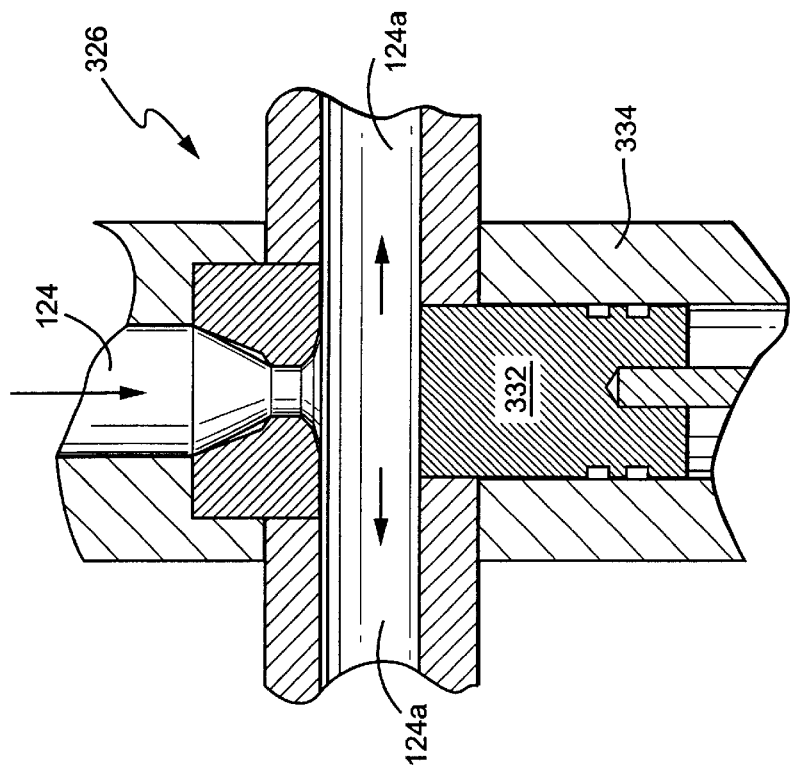
FIG. 6 is an enlarged elevational view in section of a second embodiment of a valve construction for the supplemental exhaust channel, showing the valve member in a fully closed position.
Figure 7:
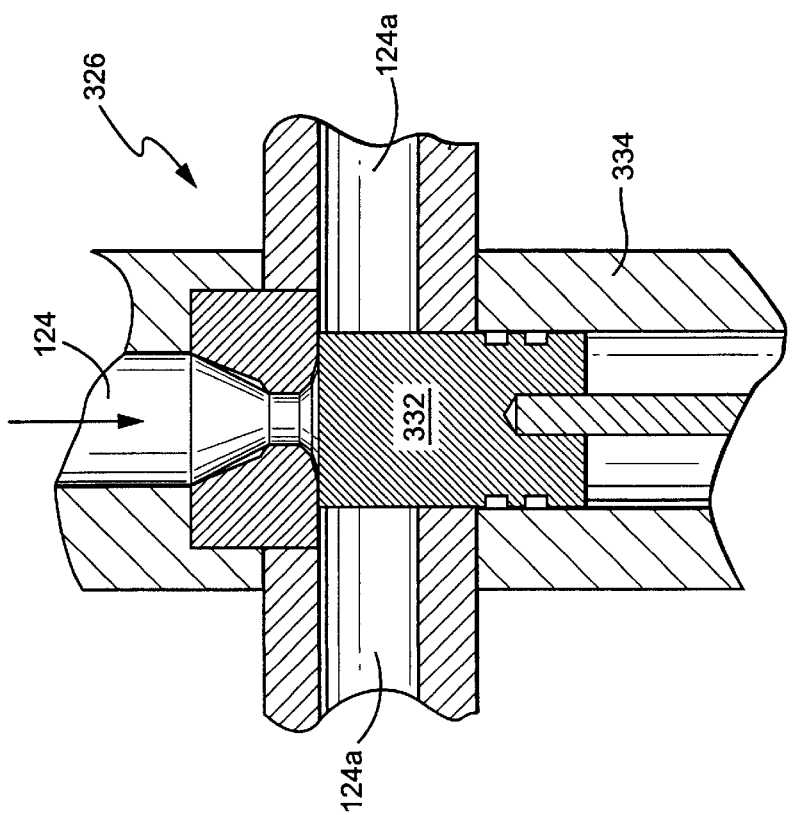
FIG. 7 is a sectional view similar to that of FIG. 6, showing the valve member in a fully open position.

FIGS. 6 and 7 illustrate a second embodiment of an exhaust valve 326 for controlling the size of the supplemental exhaust channel 124 shown in FIG. 2. The valve 326 comprises a piston or valve member 332 that is slidably mounted in a housing 334 for movement between the position in FIG. 6 wherein it closes the supplemental exhaust channel 124 and the position shown in FIG. 7 wherein it is disposed outside of the supplemental exhaust channel 124 such that it is fully open to enable flow through the lateral exhaust openings 124a.

The first embodiment of the exhaust valve 126 shown in FIGS. 4 and 5 may comprise lateral exhaust openings like the exhaust openings 124a in the second embodiment shown in FIGS. 6 and 7.

Figure 3:
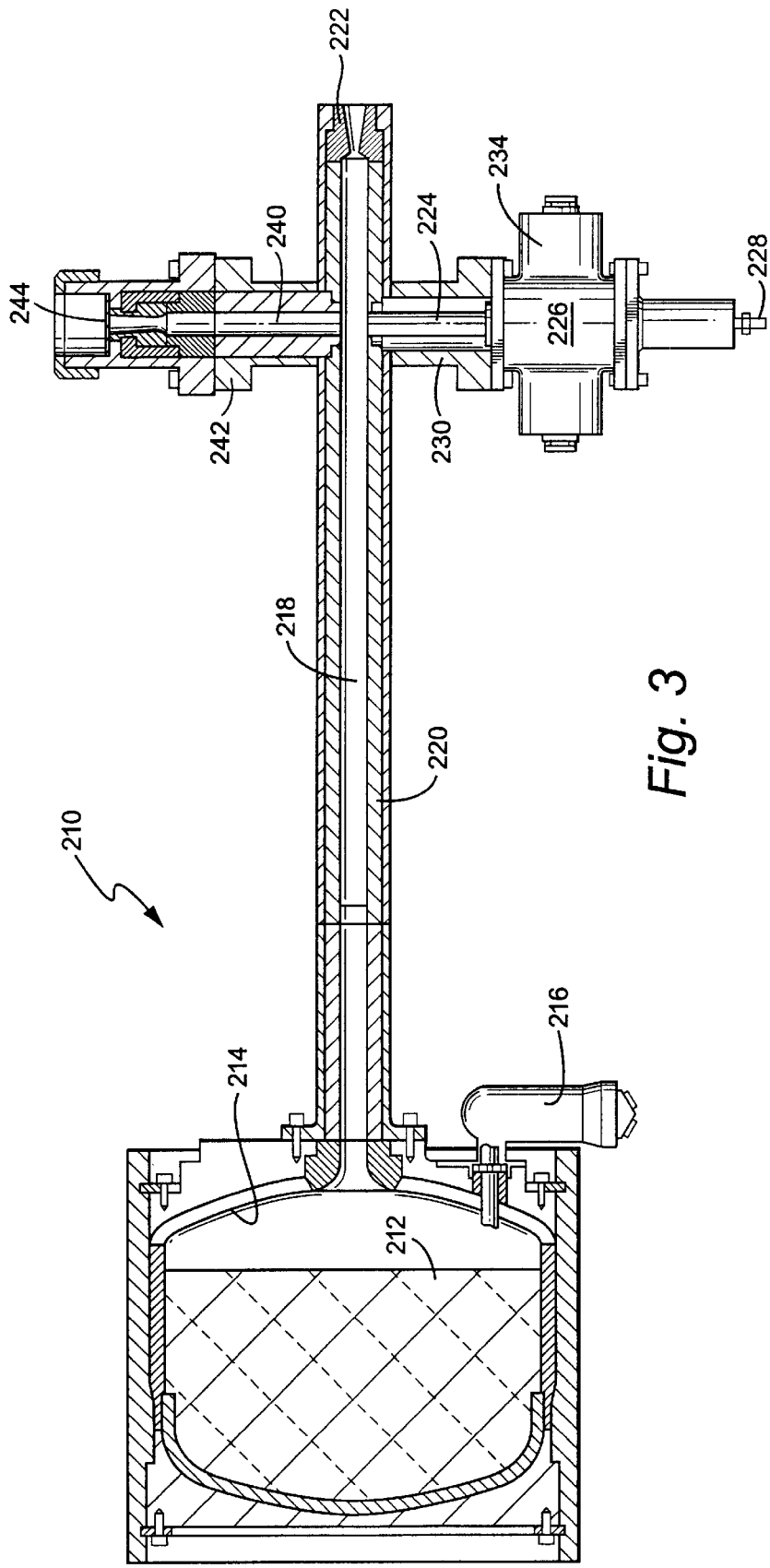
FIG. 3 is a side elevational view in section of a second embodiment of the propellant test apparatus of the present invention.

FIG. 3 illustrates a second embodiment of the propellant test apparatus 210 of the present invention that is very similar in construction and operation to the first embodiment shown in FIG. 2. The test apparatus 210 of the second embodiment comprises a combustion chamber 214 for containing a test propellant 212, an igniter 216 extending into the combustion chamber 214, a primary exhaust channel 218 in an exhaust housing 220 extending from the combustion chamber 214 to an exit nozzle 222, and a supplemental exhaust channel 224 in a housing 230 that is connected to an exhaust valve 226 for controlling the flow of exhaust gases from the supplemental exhaust channel 224 to the supplemental exhaust opening 228.

The second embodiment of the propellant test apparatus 210 further comprises an auxiliary exhaust channel 240 disposed in an auxiliary housing 242 connected to the exhaust housing 220. The inner end of the auxiliary exhaust channel 240 is in communication with the primary exhaust channel 218, and the outer end of the auxiliary exhaust channel 240 is closed by a burst disk 244 of any suitable type that is constructed to fail at a predetermined pressure. The auxiliary exhaust channel 240 and burst disk 244 serve as a safety device to vent exhaust gases from the primary exhaust channel 218 in the event the exhaust gas pressure exceeds the predetermined pressure at which the burst disk 244 will fail. In this manner, a potentially dangerous build-up of propellant exhaust gas pressure in the exhaust housing 220 is effectively prevented.

Based on the foregoing description, it will be readily seen that the new and improved solid propellant test apparatus and method of the present invention provide a simple and effective means of testing the burning characteristics of a solid propellant over a wide combustion pressure range that is independent of the burning surface area of the propellant.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. In a test apparatus for a solid propellant, comprising a combustion chamber for the solid propellant, an igniter for igniting propellant in the combustion chamber, and an exhaust housing having a primary exhaust channel extending from the combustion chamber to an exit nozzle, the improvement comprising:

a supplemental exhaust channel connected to said primary exhaust channel, and a valve for controlling the size of said supplemental exhaust channel to selectively vary the flow of propellant gases therethrough, thereby to selectively vary the combustion chamber pressure to enable the testing of the burning characteristics of the propellant over a wide pressure range independent of the burning surface area of the propellant.

2. The test apparatus of claim 1 wherein said valve is operable to move between positions wherein said supplemental exhaust channel is fully opened and fully closed.

3. The test apparatus of claim 2 wherein said supplemental exhaust channel is disposed within a supplemental exhaust housing connected to said primary exhaust housing and to said valve.

4. The test apparatus of claim 2 wherein said valve comprises a pair of opposed pistons that are movable into said supplemental exhaust channel to vary the size thereof.

5. The test apparatus of claim 2 wherein said valve comprises a piston that is movable into said supplemental exhaust channel to vary the size thereof.

6. The test apparatus of claim 3 wherein said supplemental exhaust channel comprises generally laterally aligned exhaust openings in said supplemental exhaust housing.

7. The test apparatus of claim 1 further comprising an auxiliary exhaust channel connected to said primary exhaust channel, and a burst disk disposed in said auxiliary exhaust channel and being constructed to fail at a predetermined pressure to enable exhaust gases to be vented through said auxiliary exhaust channel in the event the gas pressure in said primary exhaust channel exceeds said predetermined pressure.

8. In a method of testing a solid propellant in a combustion chamber wherein exhaust gases flow from the combustion chamber through a primary exhaust channel to an exit nozzle, the improvement comprising the steps of:

connecting a supplemental exhaust channel to the primary exhaust channel; and controlling the flow of exhaust gases through said supplemental exhaust channel to selectively vary the combustion chamber pressure to enable the testing of the burning characteristics of the propellant over a wide pressure range independent of the burning surface area of the propellant.

9. The method of claim 8 wherein the flow of exhaust gases through said supplemental exhaust channel is controlled by a valve.

10. The method of claim 8 further comprising the steps of connecting an auxiliary exhaust channel to the primary exhaust channel, and closing said auxiliary exhaust channel with a burst disk constructed to fail at a predetermined pressure to enable exhaust gases to be vented through said auxiliary exhaust channel in the event the gas pressure in the primary exhaust channel exceeds said predetermined pressure.

* * * * *